United States Patent [19]

Fitzgibbons et al.

[11] 4,328,075

[45] May 4, 1982

[54] REMOVAL OF CYANIDES FROM ACETONITRILE

[75] Inventors: William O. Fitzgibbons, Hudson; Andrew J. Barko, Lakewood, both of Ohio

[73] Assignee: Standard Oil Company

[21] Appl. No.: 152,006

[22] Filed: May 21, 1980

Related U.S. Application Data

[62] Division of Ser. No. 102,088, Dec. 10, 1979.

[51] Int. Cl.$^3$ .............................................. B01D 3/34
[52] U.S. Cl. ...................................... 203/37; 203/38; 203/54; 260/465.1; 260/465.3; 260/465.9
[58] Field of Search ................ 210/54, 59; 260/465.1, 260/465.3, 465.9; 203/28, 36, 37, 62, DIG. 3, 38, 51, 54

[56] References Cited

U.S. PATENT DOCUMENTS 3,201,451  8/1965  Idol et al. ..................... 260/465.1
3,729,413  4/1973  Csurös et al. ..................... 210/59

Primary Examiner—Frank Sever
Attorney, Agent, or Firm—David J. Untener; Herbert D. Knudsen; Larry W. Evans

[57] ABSTRACT

The present invention relates to a process for removing cyanides from a crude acetonitrile stream. Caustic and formaldehyde are added to an aqueous acetonitrile stream that contains cyanide. The formaldehyde "kills" the cyanides and provides a waste stream that can be conveniently disposed of.

11 Claims, No Drawings

REMOVAL OF CYANIDES FROM ACETONITRILE

This is a division of application Ser. No. 102,088 filed Dec. 10, 1979, now pending.

BACKGROUND OF THE INVENTION

Acetonitrile is a by-product formed during the production of acrylonitrile. The principal process for the production of acrylonitrile is by ammoxidation of propylene in the vapor phase over an oxidation catalyst. The reactor effluent typically contains anywhere from one to eight percent acetonitrile. Acrylonitrile and acetonitrile may also be produced by the reaction of hydrocyanic acid with acetylene or the reaction of acrolein with ammonia.

Acrylonitrile and acetonitrile are separated from the reactor effluent by various distillation procedures. For example, U.S. Pat. No. 3,399,120 and U.S. Pat. No. 3,264,197 discloses a method for the purification of acrylonitrile and acetonitrile by water extractive distillation.

Another byproduct formed during the above process is cyanides. These cyanides are typically found as hydrogen cyanide, but can additionally be in other forms such as cyanohydrins. When acrylonitrile and acetonitrile are separated, a percentage of the cyanides appear in the crude acetonitrile stream. These must be removed, or as known in the art, "killed" down to the ppm level for specification acetonitrile.

The prior art method of removing these cyanides has been by the addition of caustic and ferrous sulfate as described in U.S. Pat. No. 3,201,451. Prior to this addition, however, the crude acetonitrile stream resulting from the acrylonitrile operation must be azeotropicly distilled to remove a substantial portion of the water contained therein.

Ferrous sulfate and caustic react with the cyanides to form ammonium ferrocyanide. After the acetonitrile has been removed, the waste stream containing water and ammonium ferrocyanide has proven to be a difficult stream to dispose of environmentally. While free cyanides will degrade in waste treatment such as the use of bioponds, this complex cyanide will not.

The present invention's use of aldehydes, specifically formaldehyde, in place of ferrous sulfate not only removes the cyanides from the crude acetonitrile stream, but also provides a waste stream that is relatively easy to dispose of.

SUMMARY OF THE INVENTION

The invention may be stated as a process for complexing cyanides contained in an aqueous stream containing acetonitrile and cyanides by the addition of caustic and an aldehyde.

The invention may also be stated as a process for removal of cyanides from a first aqueous stream containing acetonitrile and cyanides by the steps of:

(a) adding caustic and an aldehyde to said aqueous stream to complex said cyanides; and (b) distilling said aqueous stream to obtain a second aqueous stream containing acetonitrile substantially free of cyanides.

As described in U.S. Pat. No. 3,201,451, one source of crude acetonitrile containing cyanides is an aqueous stream recovered as a byproduct of the process for the production of acrylonitrile and propylene. This byproduct may contain anywhere from about 0.2–2 wt.% but in some instances up to 8 wt.% cyanides and from about 0.05 to 1 wt.%, but in some instances up to 10 wt.% acrylonitrile. This byproduct also contains water in concentrations ranging from about 35 wt.% down to about 14 wt.%.

In order to obtain specification acetonitrile, the aqueous stream resulting from the above process containing acetonitrile and cyanides must be purified such that the final cyanide content is approximately 10 ppm or less.

A typical process for accomplishing this is by first azeotropicly distilling the aqueous stream to remove a portion of the water. The azeotrope of acetonitrile and water that contains cyanides is then mixed with caustic and the prior art ferrous sulfate. The ferrous sulfate reacts with the cyanides to produce ammonium ferrocyanide. This batch operation is then distilled with acetonitrile and water going overhead substantially free of cyanides. In the context of this invention, substantially free means an aqueous solution containing less than 25 ppm cyanides, preferably less than 10 ppm cyanides.

The present invention can utilize the above process or simplify it by replacing the ferrous sulfate with an aldehyde. In the prior art, a portion of the water contained in the crude acetonitrile stream must be removed prior to the addition of the ferrous sulfate. The more water contained in this stream, the more ferrous sulfate that must be used because of a minimum iron concentration that is necessary. In addition, the greater the water content, the more acetonitrile that is hydrolyzed during the prior art process.

By using an aldehyde, preferably formaldehyde, the initial step of water removal is not necessary. This is because the aldehyde and caustic are effective at much higher water concentrations than is the ferrous sulfate/caustic. The effect of this phenomena is that the water and cyanide removal steps can be combined into one processing step.

The caustic useful in the present invention is that known in the art. Caustics such as ammonium hydroxide, potassium hydroxide and sodium hydroxide are useful, with sodium hydroxide being preferred.

The present invention replaces the ferrous sulfate with an aldehyde such as formaldehyde, acealdehyde, or acrolein. The use of formaldehyde in the present invention is preferred.

The caustic and formaldehyde can be added in place of the caustic and ferrous sulfate without any changes in the prior art processing or equipment. Thus operating conditions known in the prior art for removal of cyanides with ferrous sulfate are applicable to the present invention and need not be described in detail.

As noted above, the caustic and aldehyde can simplify the process by eliminating the initial water removal step. This does not change the process and conditions necessary for complexing the cyanides even though the acetonitrile stream free of cyanides contains somewhat more water. Water is removed in later processing which is necessary for both the present invention and the prior art.

It is generally desirable to employ excess quantities of caustic and aldehyde to ensure removal of the cyanides. The amount of caustic used ranges from 2 to 30 gallons of 50% NaOH and 150 gal. to 15 to 60 gal. of 37% formaldehyde per thousand gal. of azeotrope treated. The actual amount of caustic and formaldehyde is dependent on the cyanide content of the azeotrope and is controlled based on specification requirements and processing costs. Typical amounts are 5 gal. of 50% NaOH and 40 gal. of 37% formaldehyde.

EXAMPLES 1-4

500 millimeters of a solution containing 60% wt.% acetonitrile, 35 wt.% water and 2.5 wt.% cyanide were charged to a 1 liter three-neck flask containing a stirrer, addition funnel, and condenser. Heat was supplied with a heating mantle around the flask. After adding the caustic and formaldehyde, the pot was refluxed for about one hour. The pot contents were then distilled overhead and condensed in 4-100 milliliter portions. Distilled water was added to maintain the liquid volume in the pot. The cyanide content of each overhead fraction was analyzed and is shown in Table I.

EXAMPLES 5-7

The procedure of Example 1 was repeated using a solution containing 0.8 wt.% cyanide.

EXAMPLES 8-10

Using the procedure of Example 1, the acetonitrile solution containing 2.5 wt.% cyanide was reacted with acrolein, acetaldehyde and paraformaldehyde respectively.

As can be seen in the Table, the use of formaldehyde, acrolein, acetaldehyde, or paraformaldehyde all serve to greatly reduce the cyanide content in the crude acetonitrile stream.

Certain handling difficulties associated with formaldehyde can be circumvented by the use of paraformaldehdye, and for this reason may be the material of choice. The aldehydes tried were effective as a cyanide kill.

The waste stream remaining after the acetonitrile and some water has been removed contains water and glycolonitrile, which is the formaldehyde cyanide complex. This complex is far more advantageous than the complex cyanide formed by ferrous sulfate because it is degradable in biopond treatment. Further, the ferrous sulfate treated waste water is a major source of COD and secondary biological treatment of this waste water results in the production of excessive amounts of ammonia. The removal of this stream serves to reduce or eliminate the need for nitrification requirements.

Finally, this stream need not be sent to a biopond for it can be safely incinerated or deep-welled.

TABLE I

| | Effect of Aldehydes on Cyanide Removal | | | | | | |
|---|---|---|---|---|---|---|---|
| | Reagent #/gal | | Cyanide Content in Overhead Fraction ppm Cyanide | | | | |
| Example | NaOH | HCHO | 0-20% | 20-40% | 40-60% | 60-80% | Average |
| 1 | .03 | .02 | 7.0 | 6.6 | 6.0 | 30 | 12.4 |
| 2 | .06 | .04 | 6.1 | 6.0 | 10 | 30 | 13 |
| 3 | .12 | .04 | 6.4 | 6 | 6 | 30 | 12 |
| 4 | .12 | .08 | 8.2 | 6 | 5.7 | 10 | 7.5 |
| 5 | .03 | .02 | 7 | 6.5 | 8.3 | 20 | 10.6 |
| 6 | .03 | .04 | 9.5 | 8.9 | 15.8 | 10.8 | 8.0 |
| 7 | .06 | .04 | 11 | 9.1 | 13 | 38 | 18 |
| 8 | .05 | (Acrolein .05) | 6.2 | 8.0 | 9.1 | 19 | 10.6 |
| 9 | .05 | (Acetaldehyde .07) | 7.1 | 9.6 | 16.6 | 28 | 15.3 |
| 10 | .05 | (Paraformaldehyde .07) | 6.4 | 6 | 6.7 | 12 | 7.8 |

We claim:

1. A process for the removal of cyanides from a first aqueous stream containing acetonitrile and cyanides by the steps of:
   (a) adding caustic and an aldehyde to said aqueous stream to complex substantially all of said cyanides to form a degradable cyanide complex of glycolonitrile; and
   (b) distilling said aqueous stream to obtain a second aqueous stream containing acetonitrile substantially free of cyanides.

2. The process of claim 1 wherein the first aqueous stream contains 0.2 to about 8 wt.% cyanides.

3. The process of claim 1 wherein the second aqueous stream contains less than 25 parts per million cyanides.

4. The process of claim 1 wherein the second aqueous stream contains less than 10 parts per million cyanides.

5. The process of claim 1 wherein the caustic is selected from the group consisting of ammonium hydroxide, potassium hydroxide and sodium hydroxide.

6. The process of claim 5 wherein the caustic is sodium hydroxide.

7. The process of claim 1 wherein the aldehyde is selected from the group consisting of formaldehyde, acetoaldehyde, acrolein and paraformaldehyde.

8. The process of claim 7 wherein the aldehyde is formaldehyde.

9. The process of claim 1 wherein the caustic is sodium hydroxide and the aldehyde is formaldehyde.

10. The process of claim 1 wherein the distilling step (b) produces a third stream containing complex cyanides.

11. The process of claim 10 wherein said third stream containing complex cyanides is passed to incineration.

* * * * *